United States Patent
Zur

(10) Patent No.: US 11,132,794 B2
(45) Date of Patent: *Sep. 28, 2021

(54) SYSTEM AND METHOD FOR DETECTION OF SUSPICIOUS TISSUE REGIONS IN AN ENDOSCOPIC PROCEDURE

(71) Applicant: Magentiq Eye Ltd., Haifa (IL)

(72) Inventor: Dror Zur, Haifa (IL)

(73) Assignee: Magentiq Eye Ltd.

( * ) Notice: Subject to any disclaimer, the term of this patent is extended or adjusted under 35 U.S.C. 154(b) by 0 days.

This patent is subject to a terminal disclaimer.

(21) Appl. No.: 16/672,747

(22) Filed: Nov. 4, 2019

(65) Prior Publication Data
US 2020/0074629 A1    Mar. 5, 2020

Related U.S. Application Data

(63) Continuation of application No. 15/758,679, filed as application No. PCT/IL2016/050998 on Sep. 8, 2016, now Pat. No. 10,510,144.

(Continued)

(51) Int. Cl.
*G06K 9/00*    (2006.01)
*G06T 7/00*    (2017.01)
(Continued)

(52) U.S. Cl.
CPC ........ *G06T 7/0012* (2013.01); *A61B 1/00009* (2013.01); *A61B 1/31* (2013.01);
(Continued)

(58) Field of Classification Search
CPC .................................................. G06T 7/0012
See application file for complete search history.

(56) References Cited

U.S. PATENT DOCUMENTS

2005/0005989 A1    3/2005  Zeng et al.
2006/0012246 A1    6/2006  Harrington et al.
(Continued)

FOREIGN PATENT DOCUMENTS

| CN | 102283626 A | 12/2011 |
|----|-------------|---------|
| CN | 103984953 A | 8/2014  |
| CN | 103984957 A | 8/2014  |

OTHER PUBLICATIONS

Magoulas et al (NPL "Neural network-based colonoscopic diagnosis using online learning and differential evolution", Elsevier, Applied Soft Computing 4 (2004) 369-379) (Year: 2004).*

(Continued)

*Primary Examiner* — Oneal R Mistry
(74) *Attorney, Agent, or Firm* — Emerson, Thomson & Bennett, LLC; Roger D. Emerson; Peter R. Detorre

(57) ABSTRACT

An image processing system connected to an endoscope and processing in real-time endoscopic images to identify suspicious tissues such as polyps or cancer. The system applies preprocessing tools to clean the received images and then applies in parallel a plurality of detectors both conventional detectors and models of supervised machine learning-based detectors. A post processing is also applied in order select the regions which are most probable to be suspicious among the detected regions. Frames identified as showing suspicious tissues can be marked on an output video display. Optionally, the size, type and boundaries of the suspected tissue can also be identified and marked.

19 Claims, 8 Drawing Sheets

Related U.S. Application Data

(60) Provisional application No. 62/216,391, filed on Sep. 10, 2015.

(51) Int. Cl.
*A61B 1/00* (2006.01)
*A61B 1/31* (2006.01)
*G06T 7/246* (2017.01)

(52) U.S. Cl.
CPC .... *G06T 7/246* (2017.01); *G06T 2207/10016* (2013.01); *G06T 2207/10028* (2013.01); *G06T 2207/10068* (2013.01); *G06T 2207/20084* (2013.01); *G06T 2207/30028* (2013.01); *G06T 2207/30032* (2013.01); *G06T 2207/30096* (2013.01)

(56) References Cited

U.S. PATENT DOCUMENTS

| | | | |
|---|---|---|---|
| 2007/0003640 | A1 | 2/2007 | Chaill et al. |
| 2008/0005859 | A1 | 3/2008 | Gu et al. |
| 2008/0058593 | A1* | 3/2008 | Gu .................. G06T 5/006 600/109 |
| 2009/0007531 | A1 | 3/2009 | Wild et al. |
| 2009/0017187 | A1 | 7/2009 | Zhang et al. |
| 2009/0252393 | A1* | 10/2009 | Agliozzo ........... G06T 7/0012 382/131 |
| 2010/0246912 | A1* | 9/2010 | Periaswamy ........... G06K 9/00 382/131 |
| 2012/0004129 | A1 | 2/2012 | Perelaman |
| 2012/0006916 | A1 | 3/2012 | Liu et al. |
| 2012/0031642 | A1 | 12/2012 | Kumer et al. |
| 2015/0006585 | A1 | 3/2015 | Jia et al. |
| 2015/0065850 | A1 | 3/2015 | Jia et al. |

OTHER PUBLICATIONS

Tajbakshsh et al. (NPL "A Comprehensive Computer Aided Polyp Detection Ssystem for Colonoscopy Videos", Information Processing in Medical Imaging: Proceedings of the Conference Jul. 2015, DOI: 10.1007/978-3-319-19992-4_25 ) (Year: 2015).*

Alexandre et al; "Polyp Detection in Endoscopic Video Using SVMs" European Conference on Principles of Data Mining and Knowledge Discovery. (2007).

Bernal et al; "Towards Intelligent Systems for Colonoscopy" Colonoscopy. (2011).

Tjoa et al; "Feature extraction for the analysis of colon status from the endoscopic images" BioMedical Engineering OnLine 2(1):9 pp. 1-17.(2003).

Zheng et al; "A fusion-based clinical decision support for disease diagnosis from endoscopic images" Computers in Biology and Medicine vol. 35, Issue 3,pp. 259-274. (2005).

Shinya et al.; "Morphology, anatomic distribution and cancer potential of colonic polyps" Annals of surgery, 190(6), 679. (1979).

Vincent "Morphological grayscale reconstruction in image analysis: applications and efficient algorithms". Image Processing, IEEE Transactions on, 2(2), pp. 176-201. (1993).

Bresson et al.; "Fast dual minimization of the vectorial total variation norm and applications to color image processing". Inverse Problems and Imaging, 2(4), pp. 455-484. (2008).

Nan "Multisensor Image Fusion Based on Tree-Structure Wavelet Decomposition " Journal of Infrared and Millimeter Waves, 3, 013; (2001).

NAbhyankar et al.; "Iris quality assessment and bi-orthogonal wavelet based encoding for recognition". Pattern Recognition, 42(9), pp. 1878-1894. (2009).

Tong et al.; "Synthesis of bidirectional texture functions on arbitrary surfaces". In ACM Transactions on Graphics (TOG) (vol. 21, No. 3, pp. 665-672). (2002).

Koenderink et al.; "Affine structure from motion".JOSA A, 8(2), 377-385) (1991).

Scharstein et al.; "A taxonomy and evaluation of dense two-frame stereo correspondence algorithms" International journal of computer vision, 47(1-3),pp. 7-42. (2002).

Laveau et al.; "3-D scene representation as a collection of images. In Pattern Recognition", 1994. Vol. 1-Conference A: Computer Vision & Image Processing., Proceedings of the 12th IAPR International Conference on vol. 1, pp. 689-691. (1994).

Lorenzo et al."Learning non-rigid 3d shape from 2d motion." Advances in Neural Information Processing Systems. (2003).

Jorge Bernal et al., "Towards Intelligent System for Colonoscopy", Computer Vision Center and Computer Science Department, www.intechopen.com, Aug. 29, 2011, pp. 245-270, 29 pages.

* cited by examiner

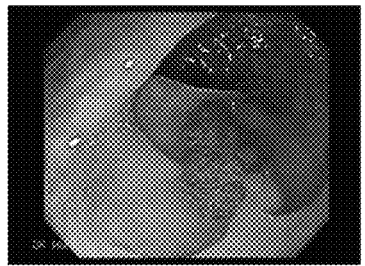
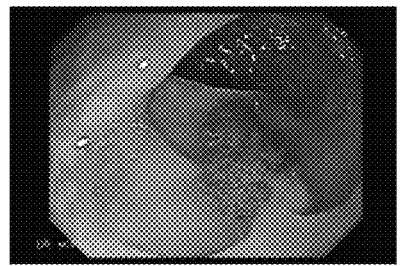
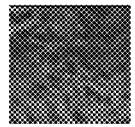
Fig. 5A
Fig. 5B
Fig. 5C
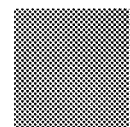
Fig. 5D
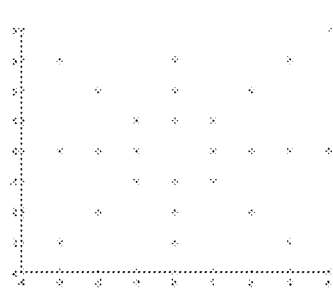
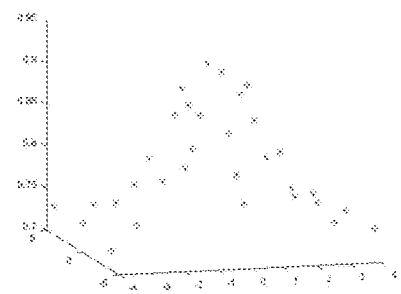
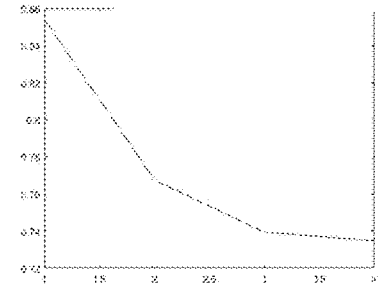
Fig. 5E
Fig. 5F
Fig. 5G
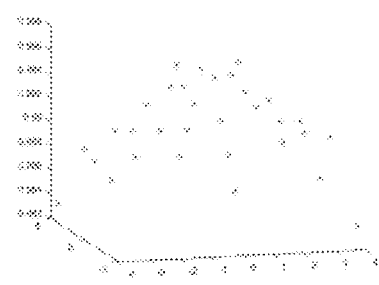
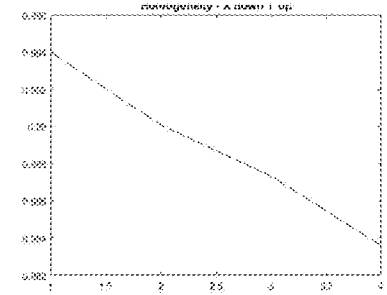
Fig. 5H
Fig. 5I

SYSTEM AND METHOD FOR DETECTION OF SUSPICIOUS TISSUE REGIONS IN AN ENDOSCOPIC PROCEDURE

DETAILS OF RELATED APPLICATIONS

This application is continuation in-part of U.S. patent application Ser. No. 15/758,679 filed on Mar. 8, 2018, a national stage application under 35 U.S.C. § 371 of PCT/IL2016/050998 filed on 8 Sep. 2016 and subsequently published as WO/2017/042812 on 16 Mar. 2017, said PCT application claiming the benefit of U.S. provisional application 62/216,391 filed on 10 Sep. 2015 according to 35 U.S.C. § 119 (e).

TECHNICAL FIELD

The present invention relates to image processing in general and in particular to a system and method for detecting suspicious regions in an endoscopic procedure.

BACKGROUND ART

An endoscopic procedure means searching and screening inside the human body by means of a medical device (the endoscope) at a hollow organ or a cavity of the body for medical purposes. Unlike most other medical imaging devices, endoscopes are inserted directly into the organ, and usually use an optical camera in the visible frequencies, or near visible frequencies (such as infra-red beams) in order to produce images and video frames from within the organ. Usually, the endoscopic procedure comes to test whether there are suspicious local regions in the tested organ, such as polyps, tumor, or evidence of cancerous cells.

A colonoscopy procedure is an endoscopic test of the large bowel (large intestine) and the distal part of the small bowel with an optical camera (usually with a CCD or CMOS camera) on an optic fiber or a flexible tube passed through the anus. It provides a visual diagnosis (e.g. ulceration, polyps) and provides the opportunity for biopsy or removal of suspected colorectal cancer lesions.

The main interest in Colonoscopy for the general public is removal of polyps as small as one millimeter (mm) or less. Once polyps are removed, they can be studied with the aid of a microscope to determine if they are precancerous or not. It takes 15 years or fewer for a polyp to turn cancerous.

The American Cancer Society "Guidelines for the Early Detection of Cancer" recommends, beginning at age 50, both men and women to undergo Flexible Sigmoidoscopy (minimally invasive examination of the large intestine from the rectum through the last part of the colon) every 5 years and Colonoscopy every 10 years.

A polyp is usually defined as a growth of excess of tissue that can develop into cancer. If a polyp is found, it can be removed by one of several techniques. Regarding shape, polyps are usually categorized into two types: pedunculated (see FIG. 1A), and sessile (see FIG. 1B). A pedunculated polyp looks like a mushroom, and a sessile polyp looks like a bump, or can be even flat on the colon tissue. The polyps can vary in size from a few centimeters, to a few millimeters, and can be even less than 2 mm or 1 mm in size. It is more difficult to detect small polyps (less than 6 mm) than large polyps, sessile are more difficult to detect than pedunculated since they are less salient form the colon tissue. Flat polyps are more difficult to detect than bump polyps, and very small (less than 2 mm) flat polyps are usually the most difficult to detect. It is important to detect even small polyps, since once they are detected, even if not suspicious as cancerous, the physician will ask the patient to come back for repeated examination in about 1 or 2 or 3 years (depending on the type and size of polyp) in order to follow up on those polyps.

The two main common types of polyps are hyperplastic polyps and adenoma polyps. The hyperplastic polyps are not at risk for cancer. The adenoma is thought to be the main cause for most of colon cancer cases, although most adenomas never become cancers. The physician usually cannot detect the type of polyp visually, and therefore the suspicious polyps are usually removed (unless they are very small) and are taken to a histology examination under a microscope. It's impossible to tell which adenomatous polyps will become cancers, but larger polyps are more likely to become cancers and some of the largest ones (those larger than 2.5 cm) can already contain small areas of cancer.

The device used for colonoscopy investigation procedures usually comprises 3 parts: 1) The endoscope which is the unit inserted into the colon (at least its distal part); 2) A control at the proximal part which helps guiding the endoscope in the colon; and a computerized external unit connected to the video output of the endoscope, receiving images and video frames from the colon. The unit usually includes a graphic processor to process and display the best possible images on an attached screen. The computerized unit usually also has additional external video outputs to which the processed video frames are passed in addition to the main video output which is destined for the main screen of the device.

Usually, a colonoscopy test is performed after the colon has been evacuated, usually via a cluster. There are some alternatives procedures such as X-ray Virtual Colonoscopy, in-vivo Ultrasound colonoscopy, in which evacuation is not required.

The colonoscopy procedure is mainly a screening test (a test for detection, preferably early detection, of a disease or a chance to have a disease). While the physician inserts the endoscope into the colon, he/she navigates it to its final destination (the farthest location, from the rectum, in the colon which he/she plans to reach with the distal part of the endoscope). During this navigation the physician looks for suspicious polyps in the colon, and if found, the physician then considers immediate removal of the polyp with a special tool which can be inserted to the colon with the optical endoscope. However, the main search and detection for suspicious polyps is done during the pull-out of the endoscope from the colon, since then the physician can be concentrated in this search without taking care for the navigation process (during the pull-out the endoscope just follow the tubular structure of the colon).

In addition to the challenge of detecting small and flat polyps, or polyps which are similar in texture and color to the regular colon tissue, one of the main difficulties in a regular colonoscopy procedure is the detection of polyps which are hidden behind concealed parts of the colon folds (polyps to which the endoscope camera has no direct line of sight). To overcome this difficulty, several tools started lately to be developed, such as an endoscope with additional cameras looking backwards, endoscopes with cameras which can view to the side or have optics which enables them to look backwards, and special balloon which is added to the endoscope in order to unfold the colon folds in the camera region.

In some back to back tests which were done with regular colonoscopy tests followed by a test of one of these techniques to see also the hidden polyps, it was found that regular colonoscopy tests miss up to 28% of all polyps and up to 24% of the adenoma polyps which are considered more dangerous regarding causes for cancer. These findings enhance the importance of developing tools that would help the physician to locate more suspicious tissues and polyps in the endoscopic screening tests with a higher precision rate and accuracy rate.

SUMMARY OF INVENTION

The present invention relates to an image processing system connected to the video output of an endoscopy device during an endoscopic procedure, comprising: at least one processor; and at least one memory communicatively coupled to the at least one processor comprising computer-readable instructions that when executed by the at least one processor cause the image processing and machine learning system to implement a method of detecting in real-time suspicious regions in endoscopic video images produced by the endoscopy device, the method comprising performing the following steps on a plurality of successive video frames:

(i) applying on each of the video frames or portions of said frames a deep machine-learning-based detection networks process comprising one or more models of general type of Detection Convolutional Neural Network (Detection CNN), Regional CNN (RCNN), Faster Regional CNN (FRCNN), You Only Look Once (YOLO) CNN, Small Data Driven (SDD) CNN, and Patch-Wise Classification CNN followed by post processing of region or blob detection, wherein each model receives as input color channels of original frames or images resulting from the processing of said conventional algorithms or three successive frames; or any combination thereof, wherein the determination to identify an area as a suspicious region takes into account the identification of that region in a predetermined number of successive frames;

(ii) receiving the results of (i) and reaching a final decision about the suspicious regions existence and location in the frame according to one or more predetermined rules, including rules which based on spatial and temporal analysis; and (iii) identifying one or more video frames as containing one or more suspicious areas and pointing out the suspicious areas' locations in each frame.

In some embodiments, the systems further comprises the step of applying on each of said video frames or portions of said frames a deep machine-learning-based detection networks process comprising one or more models of general type of Segmentation Convolutional Neural Network (Segmentation CNN), Mask RCNN, Semantic Segmentation CNN such as DeepLab, Fully Convolutional CNN such as UNET, where the location of each suspicious area is defined by the bounding box of the segmentation of the suspicious area, and the suggested resection contour of each suspicious area is based on the contour of the segmentation of the suspicious area.

In some embodiments, 3 conventional detectors and 2 models of machine learning-based detectors are applied and the location of suspicious areas is identified in said one or more video frames.

In some embodiments, the boundaries of suspicious areas are identified.

In some embodiments, the method further comprises the step of marking the suspicious area using an overlay marking on a dedicated display area.

In some embodiments, the method further comprises performing one or more of the following steps:

(i) removing from each frame peripheral regions outside the visual feed of the endoscope camera;

(ii) identifying and removing feces regions in a frame;

(iii) identifying areas with liquids in each frame or portion of frame and removing these areas or the whole frame from further processing;

(iv) identifying surgical tools in each frame or portion of frame and removing these areas or the whole frame from further processing; and (v) identifying blurry regions in each frame or portion of frame and removing these a In some embodiments, the marking comprise marking the type and/or size and/or confidence level of the suspicious region by a color marking or additional marking attributes such as dashed/not-dashed contour or the level of transparency of the color of the marked region.

In some embodiments, the existence of suspicious regions is signaled by an audio signal.

In some embodiments, different audio signals are produced depending on the size and type of the suspicious region.

In some embodiments, the method further comprises the step of calculating the size of the suspicious region.

In some embodiments, the method further comprises the step of classifying the suspicious regions according to predefined types.

In some embodiments, the method further comprises the step of tracking the endoscope tip movements according to the changes in the images of successive frames of the video stream which comes from the camera at the endoscope tip, and according the automatic registration between these successive images, and, by using the sequence of registered images, also calculating the portion of the internal part of the colon which was covered by the camera's visual field.

In some embodiments, the tracking results are incorporated in the temporal analysis of the final decision in order to improve the confidence of the detection of the suspicious areas.

In some embodiments, the method further comprises the step of registering a specific location of the endoscope tip by a user landmark and signaling when the endoscope tip is returning to the landmark location.

In some embodiments, the method further comprises the step of identifying if a suspicious region was treated or examined according to the time it was identified along successive frames, and if surgical tools were identified in said successive frames.

In some embodiments, the method further comprises the step where instead of user landmark, the location of the endoscope tip, when a suspicious region is detected but not treated, is registered, and signaling when the endoscope tip is returned to this location.

In some embodiments, suspicious regions, frames with suspicious region, and irrelevant frames are identified in an off-line recorded video.

In some embodiments, the method further comprises the step of calculating statistics regarding the endoscopic procedure.

In some embodiments, the statistics comprise the total time of the procedure, time to the cecum and from the cecum, how many suspicious regions were detected, and how many suspicious regions were removed during the procedure.

In some embodiments, the method further comprises the step of frame-freezing a suspicious region even after the endoscope proceeded from said suspicious region location.

In some embodiments, the deep machine-learning-based networks process uses training on non-endoscopic images by using a fine-tuning algorithm on the deep networks layers with emphasis on fine tuning of the semantic layers in order to the detect if the frame contains suspicious regions and the location and boundaries of those suspicious regions.

In some embodiments, the deep machine-learning-based networks process applies a combination and integration of said deep networks, in a hierarchical manner, and/or, when each of deep networks is trained for a specific internal purpose such as filtering unfocused or irrelevant frames, detecting and segmenting lumen regions, detecting and segmenting feces regions, detecting and segmenting tools regions, detecting and segmenting liquid regions, detecting only if the frames contains suspicious regions, detecting only the location of the boundary of the suspicious region in the frame, detecting the central location of the suspicious region in the frame, or any combination thereof in order to the detect if the frame contains suspicious regions and the location and boundaries of those suspicious regions. The system according to claim 1, wherein In some embodiments, the method further comprises the step of dividing each video frame into overlapping patches.

In some embodiments, the Decision Trees-based process is Random Forest.

In some embodiments, the conventional and machine learning detectors produce confidence values for their results.

In some embodiments, the one or more predetermined final decision rules comprise naïve, redundant or simple decision making such as taking the most sever decision or the most confident decision of the detectors and classifiers (sections viii and ix of claim 1), or checking the overlap level of the detected regions, or decision making based on statistical calculations or supervised machine learning methods such as decision tree by using the results of the detectors and classifier on a given and input controlled dataset with ground truth data, feeding all the regions which were detected by the detectors and classifiers with their locations as image patches into a CNN or any combination thereof.

In some embodiments, the method further comprises the step of identifying blood vessels in order to eliminate them from the option to be included in suspicious regions (many type of suspicious regions cannot include blood vessels).

In some embodiments, removing from each frame peripheral regions outside the visual feed of the endoscope camera is done by finding uniform color and low intensity regions at the peripheral part of the frame and using a region growth algorithm and morphological verification criteria.

In some embodiments, lumen regions are identified only if their size is at least 0.2% of the total pixel size of the frame.

In some embodiments, lumen regions are identified only if their saturation value is less than 0.1 on a scale of 0 to 1.

In some embodiments, feces regions are identified by identifying yellowish regions with a morphology of stain which are not bulging from the surrounding surface where thresholds and limits of the intensity, color and saturation for identifying such regions are adaptively calculated.

In some embodiments, occurrences in a frame of the endoscope internal side of the tip are identified by finding uniform color, low saturation and high intensity regions at the peripheral part of the frame where thresholds and limits of the intensity, color and saturation for this type of detection and segmentation are adaptively calculated.

In some embodiments, liquids in a frame are identified by finding white-grayish color and low saturation regions and using morphological criteria, where thresholds and limits of the color and saturation for this type of detection and segmentation are adaptively calculated.

In some embodiments, when liquids are identified in frame either the liquids area is removed from processing or the entire frame is removed from processing.

In some embodiments, the method further comprises the step of identifying reflections in each frame or portion of frame and creating additional accompanying image in which each reflection is replaced with the surrounding intensity, colors and texture. Reflections increase the chances of finding a polyp in the image.

In some embodiments, the method further comprises the step of identifying blood vessels in each frame or portion of frame and creating additional accompanying image in which each blood vessel occurrence is replaced with the surrounding intensity, colors and texture. Identifying blood vessels reduce the chances of finding a nearby polyp in the image.

In some embodiments, identifying, surgical tools in each frame or portion of frame is achieved by using criteria of color, saturation, and 2D and 3D based morphology.

In some embodiments, identifying blurry regions in each frame or portion of frame is achieved by criteria calculated on the gradients of the image, and in case the sum of the areas of these regions is larger than a predetermined value, removing the whole frame from further processing.

In some embodiments, the method further comprises additional conventional detectors comprising: shape detection and segmentation; motion analysis; and comparison with one or more image templates.

In some embodiments, the determination to identify an area as a suspicious region takes into account morphological criteria.

In some embodiments, the determination to identify an area as a suspicious region takes into account morphological criteria.

In some embodiments, the id SVM based process and said Decision Trees-based process receive as input feature vector and parameters calculated by the conventional algorithms.

In some embodiments, the SVM based process and said Decision Trees-based process, process a frame in order to detect characteristics which are typical to polyps and to classify frames accordingly.

In some embodiments, data augmentation is used for deep machine-learning-based networks processes in order to use polyp and background characteristics in order to create from each frame or patch several additional frames to be processed by deep learning networks.

In some embodiments, the method further comprises the step of adding pre-extracted features provided by the conventional algorithms into the fully connected feature layers of said deep machine-learning-based networks as additional features of said layers.

In some embodiments, the determination by the deep machine-learning-based networks processes to identify an area as a suspicious region takes into account morphological criteria.

In some embodiments, the suspicious regions are polyps or cancerous regions.

In another aspect, the present invention relates to an image processing system connected to the video output of an endoscopy device during a colonoscopy procedure, comprising: at least one processor; and at least one memory communicatively coupled to the at least one processor comprising computer-readable instructions that when executed by the at least one processor cause the image processing and machine learning system to implement a method of detecting in real-time polyps in endoscopic video images produced by the endoscopy device, the method comprising performing the following steps on a plurality of successive video frames:

(iv) applying on each of the video frames or portions of said frames a deep machine-learning-based detection networks process comprising one or more models of general type of Detection Convolutional Neural Network (Detection CNN), Regional CNN (RCNN), Faster Regional CNN (FRCNN), You Only Look Once (YOLO) CNN, Small Data Driven (SDD) CNN, and Patch-Wise Classification CNN followed by post processing of region or blob detection, wherein each model receives as input color channels of original frames or images resulting from the processing of said conventional algorithms or three successive frames; or any combination thereof, wherein the determination to identify an area as a suspicious region takes into account the identification of that region in a predetermined number of successive frames;

(v) receiving the results of (i) and reaching a final decision about the suspicious regions existence and location in the frame according to one or more predetermined rules, including rules which based on spatial and temporal analysis; and (vi) identifying one or more video frames as containing one or more suspicious areas and pointing out the suspicious areas' locations in each frame.

In some embodiments, the systems further comprises the step of applying on each of said video frames or portions of said frames a deep machine-learning-based detection networks process comprising one or more models of general type of Segmentation Convolutional Neural Network (Segmentation CNN), Mask RCNN, Semantic Segmentation CNN such as DeepLab, Fully Convolutional CNN such as UNET, where the location of each suspicious area is defined by the bounding box of the segmentation of the suspicious area, and the suggested resection contour of each suspicious area is based on the contour of the segmentation of the suspicious area.

BRIEF DESCRIPTION OF DRAWINGS

FIG. 5A-5I show an example of the difference in the texture homogeneity calculation, between a polyp region and a non-polyp region—this is one of the texture calculations which use to detect polyp regions. FIG. 5A is the input image, FIG. 5B is the gray level presentation of the input image, FIG. 5C is a patch from the polyp region and FIG. 5D is a patch of a non-polyp regions, FIG. 5E is the locations in the patches above where co-occurrence matrix (from which the homogeneity calculation is derived) is calculated, FIG. 5F is the homogeneity values at those location for the polyp patch, FIG. 5G is the homogeneity values along a straight line which goes over such locations for the polyp patch, FIG. 5H is the homogeneity values at those location for the non-polyp patch, FIG. 5I is the homogeneity values along a straight line which goes over such locations for the non-polyp patch. The comparisons between FIG. 5F and FIG. 5H, and between FIG. 5G and FIG. 5I show the difference between the homogeneity of the polyp and the non-polyp patches, which used in order to differentiate them in practice.

FIG. 7A is the original image, FIG. 7B is the original image without the shading (was omitted by a Retinex algorithm), FIG. 7C is the color difference between the original image and image without the shading and FIG. 7D is the gray level difference between the original image and the image without the shading, FIG. 7E is a binarization of this difference (of the shading element in the image) and FIG. 7F is the sign of the region, that was detected according to further evaluation of the binary image for pattern which can correspond to closed shape bumped polyp, on the original image.

MODES FOR CARRYING OUT THE INVENTION

Figure 1A:
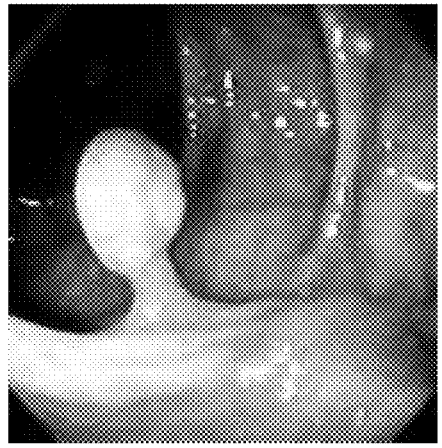
FIGS. 1A-1B show two examples of colon polyps, a polyp on a stem (also called pedunculated polyp) in FIG. 1A, and a relatively flat polyp in FIG. 1B.

In the following detailed description of various embodiments, reference is made to the accompanying drawings that form a part thereof, and in which are shown by way of illustration specific embodiments in which the invention may be practiced. It is understood that other embodiments may be utilized and structural changes may be made without departing from the scope of the present invention.

The system of the invention is adapted for automatically detecting the presence and location of suspicious tissue regions in endoscopic images. For clarity purposes, the disclosure details automatically detecting polyps in a colonoscopy procedure, though any person skilled in the art will immediately understand how to customize the system and method described to identify suspicious tissue regions in images of other endoscopic procedures in other cavities of the body such as a sigmoidoscopy examination, or any other endoscopic procedure.

The system and method of the invention examines endoscopic images captured in the colon, and identify the location of different types of suspicious tissues, in this case polyp. Polyps can be: large/medium polyps, small polyps, and most importantly to detect are flat polyps. Besides polyps, the system can identify other suspicious tissues in any part or side of the folds of the colon. The detection of polyps or other suspicious tissues is performed online while the colonoscopy procedure, sigmoidoscopy examination etc. is actually performed. Alternatively, the system can review endoscopic images offline (on a video that recorded during the endoscopic procedure).

The system of the invention is an image processing system typically connected to the video output of an endoscopy device during a colonoscopy procedure, though the system can also process off-line a video output of a previously recorded endoscopic procedure.

The video frames which are directly produced by the endoscope's camera contain many frames or regions in frames that may be blurry, not in focus or contain unnecessary information for the detection of suspicious tissues. Thus, in order to increase the overall detection rate and speed the process, an endoscopic-oriented filtering algorithm is applied for regions with low information in periphery, inside the image (dark regions), and for blurry (not-in focus) frames or regions, in order to enhance and speed the processing of the image processing system of the invention. The peripheral low information regions are identified by finding relatively uniform (with a low standard deviation) color and low intensity regions at the peripheral part of the frame and then using a region growth algorithm and morphological verification criteria to discover and find the limits of that region. Removing the low information regions inside the image (the Lumen regions) is achieved by identifying low intensity regions by using adaptive threshold (according the average and the standard deviation of the intensity in the image) and which have high enough compactness (the ration between the area and the area of its convex hull). This computation is done patch-wise, namely, the average and standard deviation of the intensity of each patch is compared with overall average and standard deviation of the intensity of the whole image. The blurry regions are identified by criteria calculated on the gradients of the image, and in case the sum of the areas of these regions is large enough, the removing the whole frame from further processing. In this way, when the surroundings of a suspicious region is blurry but the region of interest is sharp enough (occurs in many cases of endoscopic images), then this region of interest is kept for further processing. This calculation is also done by an adaptive threshold (according to the average and the standard deviation of the gradients of the image), and is calculated patch-wise, namely, the average and the standard deviation of gradients of each patch are compared with the overall average and standard deviation of the whole image.

The system comprises at least one processor and at least one memory communicatively coupled to the at least one processor comprising computer-readable instructions that when executed by the at least one processor cause the image processing and machine learning system to implement a method of detecting in real-time suspicious regions in endoscopic video images produced by the endoscopy device. The method comprising performing the following steps on a plurality of successive video frames. It is not necessary to process each and every video frame, and the system can be configured to skip some frames, for example, process one frame out of three, one frame out of two, process two frames and skip four frames, or any other order. Thus the term "successive frames" as defined herein means frames that are processed in chronological order, but not necessarily frames that immediately follow each other in the video stream.

Figure 2:
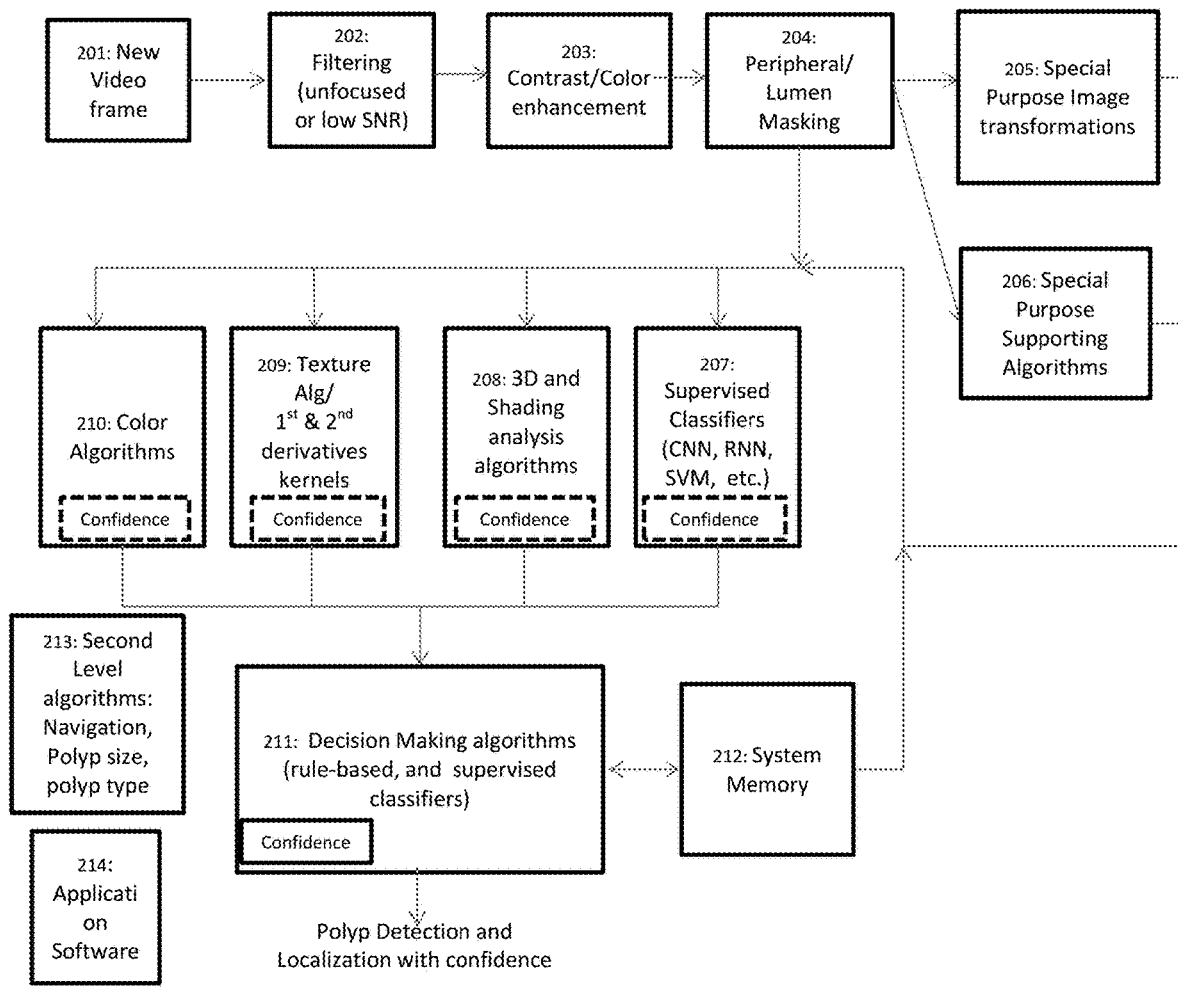
FIG. 2 illustrates an embodiment of a process/algorithmic system.

Reference is made to FIG. 2 showing an embodiment of a process/algorithmic system of the invention. In step 201, a new input video frame is received (from the Endoscope camera). In step 202, frames are filtered if they are unfocused or with low Signal to Noise Ratio (SNR). Step 203 enhances the color and contrast of the input image (frame) by expanding its dynamic range. Step 204 filters out the Lumen part (the darks areas) and peripheral part (out of the endoscope camera field of view) part from the image. Step 205 calculates special image transformations such as color transformation, edge detection, $1^{st}$ derivative transform, for the use of the algorithms to follow. Step 207 applies the supervised machine learning algorithms which classify if a frame or patch (a patch is a portion of a frame; a frame can be divided to a plurality of patches, each patch processed on its own and in consideration of other patches in the frame) contains or is included in a polyp. Step 208 analyzes the shading and the 3D structures in the image to find regions which are suspicious as polyps. Step 209 uses texture features (such as those based on co-occurrence matrix calculation) and additional features that were extracted by special purpose image transformations to detect regions which are suspicious as polyps. Step 210 clusters and analyzes the colors in the image to detect regions which are suspicious as polyps. Step 211 takes the final decision whether there is a suspicious region in the processed frame or patch, when the algorithms in steps 207 to 211 produce also a confidence level (usually between 0 and 1) for their detection or classification results. Step 212 is the system memory (over time) checking and validating the continuity of the polyp detection in successive frames. Step 213 includes satellite algorithms such as tracking, navigation, polyp size calculation, and polyp type classification and step 214 denotes the software application that runs all those algorithms together.

Initially, some preprocessing steps are performed in order to eliminate from the frames unnecessary areas thus reducing the size of the processed frames and accelerating the process time (since there's a smaller image size to process) and also increasing accuracy (as unnecessary image portions are cleaned or eliminated, so there is less potential for mistakes).

(i) Removing from each frame peripheral regions with no information. As images are rectangular by nature, and the inside of the colon is closer to the shape of a circle, there will peripheral regions with no actual value. Removing those regions is achieved by finding relatively uniform (with a low standard deviation in the range of 0.1 when each color channel range is between 0 and 1) color and low intensity regions (below 0.1, when the intensity range is between 0 to 1) at the peripheral part of the frame and then using a region growth algorithm and morphological verification criteria to discover and find the limits of that region and to disqualify regions which are too small (below 0.05% of the area of the whole image) or which have too small compactness (the ratio between their area and the area of their convex hull is less than 0.7).

(ii) Identifying and removing lumen regions in a frame by finding low intensity regions (below 0.1, when the intensity range is between 0 and 1) than in the frame;

(iii) Identifying, and removing feces regions in a frame by identifying yellowish regions with a morphology of stain which are not bulging from the surrounding surface where thresholds and limits of the intensity, color and saturation for identifying such regions are adaptively calculated.

(iv) Identifying and removing occurrences in a frame of the endoscope internal side of the tip at peripheral parts of the frame by finding relatively uniform (with a low standard deviation, namely, with a standard deviation in the range of 0.1 when each color channel range is between 0 to 1) color, low saturation (below 0.15 when the saturation range is between 0 to 1) and high intensity (above 0.85 when the intensity range is between 0 to 1) regions at the peripheral part of the frame where thresholds and limits of the intensity, color and saturation for this type of detection and segmentation are adaptively calculated.

(v) Identifying and removing areas with liquids in each frame or portion of frame by finding white-grayish color and low saturation regions and using morphological criteria, where thresholds and limits of the color and saturation for this type of detection and segmentation are adaptively calculated.

(vi) Identifying reflections in each frame or portion of frame and creating additional accompanying image in which each reflection is replaced with the surrounding intensity, colors and texture.

(vii) Identifying and removing tools in each frame or portion of frame by using criteria of color, saturation, and 2D and 3D based morphology.

The next two steps involved applying different types of detectors on the processed video frames. Depending on the machine configuration and strength, all the applied detectors below can be applied simultaneously on the processed video frame in order to gain time.

(viii) identifying and removing blurry (not in focus) regions in each frame or portion of frame by criteria calculated on the gradients of the image, and in case the sum of the areas of these regions is large enough (at least 70% of the whole image area), then removing the whole frame from further processing. In this way, when the surroundings of a suspicious region is blurry but the region of interest is sharp enough (occurs in many cases of endoscopic images), then this region of the interest would still be kept for further processing.

(ix) Applying on each of the processed video frames or portion of those frames two of the following conventional detectors. A "conventional detector" as defined herein is a detector that is not based on a supervised learning algorithm. The conventional detectors are adapted to detect (in combination with the supervised machine learning detectors and classifiers) if the video frame or part of it contain suspicious regions and the location and boundaries of those suspicious regions: color analysis; texture/edges/kernel-based extraction analysis; shading analysis; 3-dimensional (3D) image analysis; shape detection and segmentation; motion analysis; comparison with one or more image templates; or any combination thereof, wherein the determination to identify an area as a suspicious region takes into account morphological criteria, such as the area size of the region, whether it is close or reaching the border of the visual field (total area in which objects can be seen by the endoscope camera) as projected to the image, it compactness (the ratio between its area to its convex-hull area), its eccentricity (the ratio of the distance between the foci of the ellipse, that has the same second moments as the region, and its major axis length), and the identification of that region in a predetermined number of successive frames;

(x) Applying on each of the video frames or portions of the frames one of the following models of supervised machine learning-based detectors in order to classify which features and image regions are related to suspicious regions: applying a Support Vector Machine (SVM) based process; applying a Decision Trees-based process; applying a deep machine-learning-based networks process comprising models of Convolutional Neural Network (CNN), Regional CNN (RCNN), and Long-Short Term Memory Recurrent CNN (LSTM Recurrent CNN), with combination of pre-extracted features fed either into the fully connected layers of said deep machine-learning-based networks as additional feature, or into the input conventional layer as additional image channel; or any combination thereof, wherein the determination to identify an area as a suspicious region takes into account morphological criteria and the identification of that region in a predetermined number of successive frames.

(xi) Receiving the results of (viii) and (ix) and reaching a final decision about the suspicious region existence in the frame and their location according to one or more predetermined rules.

(xii) Identifying one or more video frames as containing a suspicious area.

Preprocessing Algorithms:

The preprocessing algorithms are the first algorithms which are run in parallel on the online (or offline) captured colonoscopy video frames produced by the endoscope. After the preprocessing cleanup of the video frames the resulting video frames are fed to the various detection algorithms. Below are some of the pre-processing algorithms used:

1. Signal to Noise Detection, Filtering and Improvement

Figure 3:
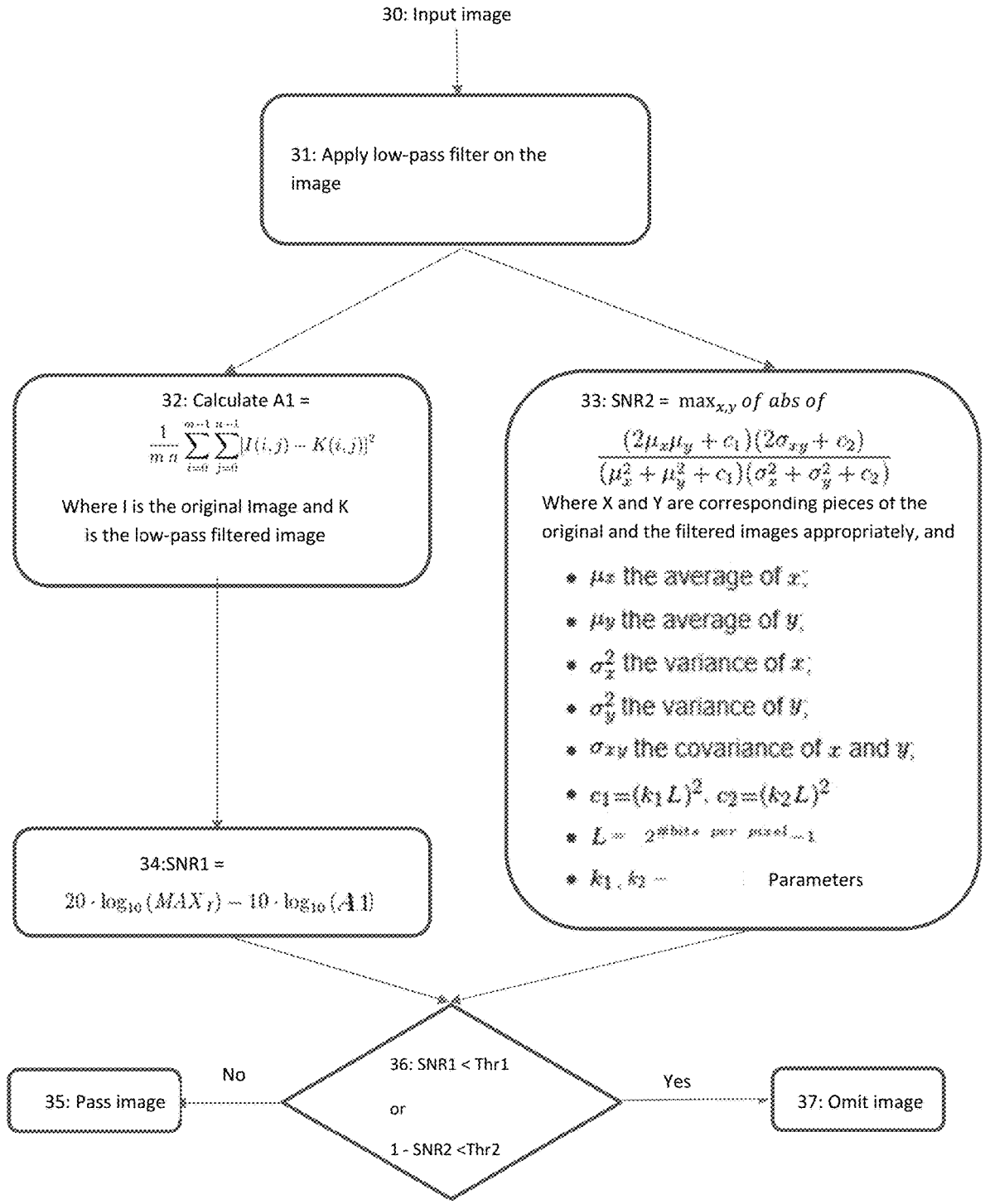
FIG. 3 is a flow chart of an embodiment of a signal to noise ratio calculation filtering algorithm.

Reference is now made to FIG. 3 illustrating a flow chart of the signal to noise ratio calculation filtering algorithm. In step 30, an input image (video frame, or a patch is received). In step 31, a low-pass filter is applied to the input image. The low-pass filter can be specific non-recursive filters such as 2D-Finite Impulse Response (FIR) or recursive filters such as 2D-Infinite Impulse Response (IIR) or by convolution with an appropriate operator such as Gaussian kernel. In step 32, the average difference between the original image and filtered image is calculated globally (all together over all the image pixels). In step 33, the first and second moments of the original and filtered image are calculated locally (calculated in patches or small pieces, 64*64 pixels for example, of the images). In step 34, the global average value is transformed to decibels unit, and in step 35 if the maximum of the local-based calculation or if the global-based calculation are below a predefined threshold (different thresholds for the left channel and the right channel, for example, 12 and 0.2 accordingly when the image intensity channel value changes between 0 to 255) then the frame is omitted (goes to step 37) and otherwise the image is passed for further processing in step 36. The specific threshold might be set in advance by a parameter, or it might be calculated adaptively according to the sequence of the input frames in order to eliminate local degradation in the input level, and it might be a combination of in-advance set threshold (such as the values mentioned here above) which can be adaptively changed according to the actual values calculated on the input sequence (for example, if the calculated values are consistently above the predefined-set thresholds, then the thresholds values might be increased).

2. Masking the Peripheral Regions (Out of Scope Field of View)

This algorithm removes the part of the image which is out of scope view (masking out the periphery) by using a combination of circular Hough transform and Random Sample Consensus (RANSAC) analysis, in order to identify the pattern of the endoscope tip and to discard its periphery which is usually dark. It applies a circular Hough transform and RANSAC algorithm which looks for correspondence with an arc pattern (part of the circle). The Hough and RANSAC algorithms are applied separately to the right side and to the left side, because the arc patterns in both sides are not necessarily symmetric, and sometimes there are even deviations from the classic arc pattern. In addition, and as an alternative, and for more complex scope patterns, a non-geometric algorithm is applied which identifies the exterior regions which in one or more of the color channels are unique, in order identify the pattern of the endoscope tip and to discard its periphery which is usually dark.

3. Masking Out the Lumen Area—the Far and Dark Center of the Colon as Seen in the Center of the Endoscope Image This algorithm also uses a combination of circular Hough transform, and RANSAC analysis, in order identify a pattern which is expected to be typical to the way the Lumen is usually seen, with the support of specific color and intensity segmentation algorithm which matches the color and intensity with which the lumen is expected to be seen—this supportive algorithm is adaptive (the color and intensity limits which the algorithm is looking to find in the lumen area is defined adaptively according to the statistics of each image or several successive images, for example, by linear combination of the average and the standard deviation of the intensity and the color channels, such as the lower limit might be the average minus half of the standard deviation and the upper limit might be the average plus the standard deviation). It applies a circular Hough algorithm and the RANSAC algorithm which looks for correspondence with circular pattern, but it allows quite significant deviations from an accurate geometric circular pattern. In addition, and for more complex patterns, a non-geometrical algorithm is applied and identifies regions in which the intensity and the saturation values are either low or included in highly narrow dynamic range, in order identify a pattern which is expected to be typical to the way the Lumen is usually seen.

4. No Focus Detection

This algorithm is based first on extracting several type of features from the image, such as edges, ridges, corners, and result of convolving the image with a combination of hessian kernels and then thresholding the result, and then by counting the number of extracted features under certain level of threshold for each type of feature, and analyzing the distribution and density of these features in image in order to decide if there enough features, if they are dense enough, and if they are distributed evenly enough in along sufficient part of the image, in order to declare the image as an image in focus. An image which is not in focus is usually discarded from further analysis in the system. The threshold for an image to be decided as in focus is statically decided according to a large set of focused images of the colon from different point of views and a smaller set of unfocused images of the colon. This threshold might be different for different endoscope cameras and might be trained offline separately for different cameras or different camera types. An alternative to this exhausting process is to use a supervised classifier in order to decide whether an image is in focus or not. In that case, the classifier (such as SVM methods or feedforward neural network with back propagation learning) would be fed, in the supervised phase, with focused and unfocused images, and then while online it will classify each input image as in-focus or unfocused. Unfocused images will be presented to the user, but would not be fed to the following processing levels of the system, and therefore no decision will be made based on these images. If a series of successive unfocused images are being fed to the system (more than 10 frames, for example), then the overlay presentation (based on the former decisions) would be stopped, and if the feeding of that unfocused frames continues (more than 20 images, for example), then the current system decision would be reset (but its history would be kept).

5. A Channel in which the Color Dominancy is Changed (Simulating the Narrow Band Imaging (NBI))

The system also uses a channel in which the color dominancy in the video frames is changed in order to make the polyp region more prominent both for subsequent processing and for alternative video display on a colonoscopy device watched by the colonoscopy procedure's operator or physician. This is achieved by changing the histogram of each color channel, for example, by a applying different historgram equalization (equalizing to different histogram pattern) to each of the color channels or by applying a shift to the hue channel in the Hue Saturation Value (HSV) format of the color image in order to change the color dominancy of the image, and thus imitating the effect of enlighting the scene by specific Narrow Band Imaging (NBI), namely buy only part of the white light frequencies. The above described techniques are preferred over just digitally filter specific colors (color frequencies) from the image, since such filtering attenuates the overall intensity of the image.

Conventional Detectors

After the preprocessing stage, the system analyzes the resulting video frames (all or a subset of all frames) by conventional and non-conventional detectors. Conventional detectors are detectors that are not based on a supervised learning algorithm.

6. Analyzing the Geometric Structure of the Lumen in Order to Detect Interference by Possibly Elevated or Prominent Polyps For each selected frame, a special algorithm looks if it can find the center of the hole of a tubular pattern of the colon (this hole is called the "Lumen", and it is possible to detect it when the endoscope camera is directed forwards or backwards, but not to the sides). The Lumen area is typically of low intensity because most of the emmitted light is not reflected back to the endoscope camera. Once the center of the hole is found (see the lumen masking algorithm in the pre-processing section), its bounding contour is corresponded, by template matching and by parametric analysis, with the pattern of possible circles, ellipses, or piecewise joined ellipses which can be detected normally in the image when the lumen of healthy and normal colon is projected to the image by the endoscope camera. If a salient deviation from these expected patterns is found, then deviated region in the image is signed and transferred with the result of the other detection algorithms (color, texture, 3D and etc.) to the rule-based decision unit to examine the possibility of being detected as a potential for a polyp.

7. 2D Edges Analysis

A further analysis is also performed on the 2D edges detected in the pre-processed image: The difference in the 3D pattern of the polyp with regards to its immediate environment creates also 2D discontinuities (2D edges) in the 2D video frame. These edges are mainly caused due to depth discontinuities (a polyp on the background of the colon surface—the polyp surface is different in color and texture) and illumination discontinuities (the polyp has different surface normal angles regarding the rest of the colon surface and therefore it reflects the light in different angles). An exhaustive 2D edge detection algorithm is used to find those edges, and post processing algorithm is used to distinguish those 2D edges from the rest of edges in the image by means closure with small radius, different direction than the rings created by the colon folds, and more.

8. Color Analysis

Tissue, which is suspected to be a polyp, usually has a different color, hue and saturation from its nearest environment, and from the regular color, hue, and saturation of the colon in general (see "Shinya, H. I. R. O. M. I., & Wolff, W. I. (1979). Morphology, anatomic distribution and cancer potential of colonic polyps. Annals of surgery, 190(6), 679"). This tissue usually tends to be more reddish, pinkish, or yellowish.

With the special artificial illumination of the endoscope, those differences are even more salient, and suspicious regions are also brighter than their environment.

An example of a color algorithm which can be used is the color segmentation algorithm which looks for those differences and detects a region (a blob) which is more reddish or pinkish or yellowish than its environment, by using specific value or range thresholding, filtering, morphologic operations and connected components analysis (see k. Vincent, L. (1993). Morphological grayscale reconstruction in image analysis: applications and efficient algorithms. Image Processing, IEEE Transactions on, 2(2), 176-201) in order to differentiate the polyps region. This technique is applied on the hue and saturation channels of the video frames, or on a combination of the RGB channels of the video frames (see 1. Bresson, X., & Chan, T. F. (2008). Fast dual minimization of the vectorial total variation norm and applications to color image processing. Inverse Problems and Imaging, 2(4), 455-484).

Another algorithm which is used to detect polyps regions is the algorithm which differentiates color regions of interest by comparing color and location statistical global data with color global data. This algorithm is built on finding regions which appear as outliers to the rest of the image when analyzing color parameters and statistics.

Figure 4:
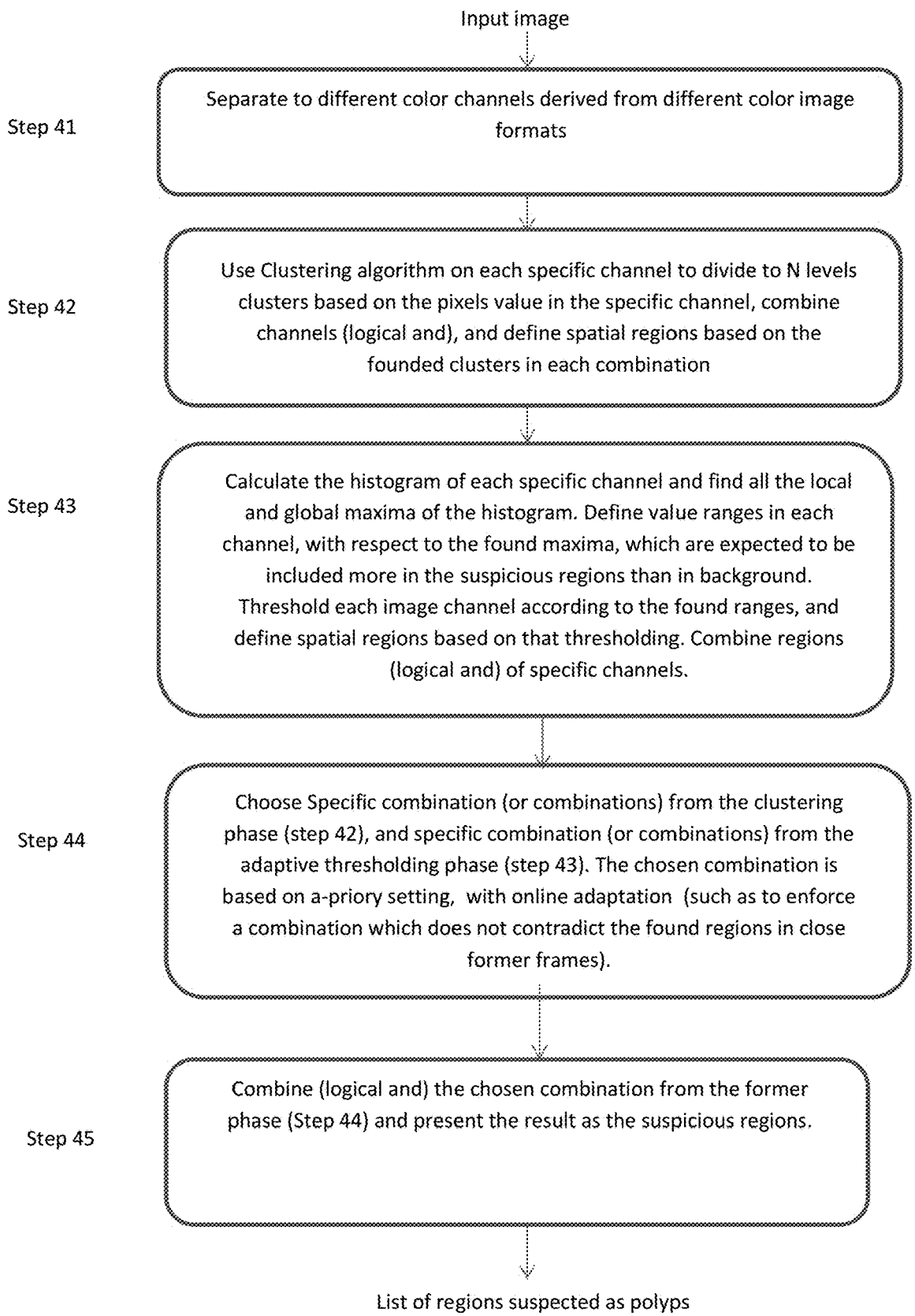
FIG. 4 shows an embodiment of a flow of the color segmentation algorithm, based on adaptive clustering and adaptive thresholding in order to detect and segment regions which are suspicious as polyps.

An example of color segmentation algorithm when the range of color is investigated in several different color channels such as Cr and Cb (from YCrCb format), A and B (from L*A*B* format), and H and S (from HSV format), and each channel, is supported and accompanied with iterative clustering algorithms (k-mean clustering, and online histogram analysis) which keep this investigation adaptive (to each new frame), and are followed with integration of the results from all the channels and decision rules to detect the suspicious regions, is presented in FIG. 4. FIG. 4 is an embodiment of the flow of the color segmentation algorithm, based on adaptive clustering and adaptive thresholding in order to detect and segment regions which are suspicious as polyps. In step 40, an input image is received. In step 41, the image is transformed to several 3 channels formats such as HSV, YCbCr, and La*b*. In step 42, the channels of those formats are used is several combinations in order to cluster the image pixels. In step 43, histograms of the different channels are calculated and analyzed in order to define regions (in the channel's range values) which might include suspicious regions. In step 44, blobs are derived from the analysis in steps 42 and 43. In step 45, those blobs are combined together and their geometry and morphology are checked in order to choose only those blob regions which are suspected as polyps.

9. Texture Analysis

Tissue, which is suspected as polyp, usually has different textural pattern from its nearest environment and from the regular textural pattern of the colon in general. Such tissue is usually rougher and has a less plain, smooth and regular pattern. Below is a more detailed overview of an example of a texture analysis algorithm.

A texture analysis algorithm which looks for those differences and detects them in several ways, uses tree-structured and several types of wavelets transforms (see m. Nan, L. S. T. W. Y. (2001). MULTISENSOR IMAGE FUSION BASED ON TREE-STRUCTURE WAVELET DECOMPOSITION [J]. Journal of Infrared and Millimeter Waves, 3, 013; and n. Abhyankar, A., & Schuckers, S. (2009). Iris quality assessment and bi-orthogonal wavelet based encoding for recognition. Pattern Recognition, 42(9), 1878-1894). It uses texture segmentation wavelets and cross-correlation kernels which are convolved over the video frames to raise a prominent and salient region and then performing thresholding, filtering, morphologic operations and connected components analysis in order to differentiate the polyps region. The cross-correlation patterns which are used, are based on an a-priory known and expected texture patterns and in appropriate scales (using scale factor correction), and some of them are based on 6 parameter bi-directional function (BTF) for texture synthesis (see refs. o. Tong, X., Zhang, J., Liu, L., Wang, X., Guo, B., & Shum, H. Y. (2002, July). Synthesis of bidirectional texture functions on arbitrary surfaces. In ACM Transactions on Graphics (TOG) (Vol. 21, No. 3, pp. 665-672). ACM).

Another texture algorithm, which is used in the system, searches for specific descriptors which are typical to a polyp texture region. These descriptors includes computation of (in the different color channels) intensity Variance, Entropy, Energy, Homogeneity, 3rd order moment, Inverse variance. Detection of typical values of these descriptors in an image region can raise the probability for polyp detection.

Also, cartoon images are produced in order to extract the texture patterns (the difference between the original image and the cartoon image) and analyze them. An analysis with the Run Length Matrix is used.

Another more specific texture algorithm that can be used is specific for polyp detection. This algorithm is based on calculation of Gray Level Co-occurrence Matrix (GLCM) over each frame, calculating some specific statistics and moments which can be derived from the co-occurrence matrix (such as correlation, entropy, energy, and homogeneity), and then finding specific characteristics in each of these moments and statistics which is typical to specific polyp type or types and not to a non-polyp region. This enables the algorithm to differentiate polyp regions from non-polyp regions. Some examples for the difference between specific polyp type characteristics and non-polyp regions appear in the graph in FIGS. 5A-5I. In the preprocessed image, a GLCM matrix is calculated, and then regions which are defined "more textural" are detected by range filtering which is a calculation of intensity max-min difference in a M×N neighborhood around the central pixel and then thresholding the results to a binary images and defining main accepted regions according to connected-components (blob) analysis. Then, specific moments and statistics are calculated in the "more textural" regions to test if they have characteristics which are typical to polyps, and some moments and statistics are calculated in sample regions from the not "more textural" area in order to verify that they do not have characteristics which are typical to polyps.

Example of differences in the homogeneity calculation between a polyp region and a non-polyp region is shown in FIGS. 5A-I. FIG. 5A shows the tested frame; FIG. 5B shows the tested frame in gray level; FIG. 5C shows the polyp region in the frame; FIG. 5D shows a non-polyp region; FIG. 5E shows the distance (in pixels) at which the co-occurrence matrix and the statistics (homogeneity in this case) are calculated for each pixels; FIG. 5F shows the average of the homogeneity calculation over the polyp region as a 2D function over the distance in pixels; FIG. 5G shows the average of the homogeneity calculation over the polyp region as a 1D function over the distance in pixels in a specific direction; FIG. 5H shows the average of the homogeneity calculation over the non-polyp region as a 2D function over the distance in pixels; and FIG. 5I shows the average of the homogeneity calculation over the non-polyp region as a 1D function over the distance in pixels in a specific direction as in FIG. 5G. It can be seen that in the polyp region the homogeneity value is lower than in the non-polyp region and (more typically than that) its values are decreasing more rapidly as the distance from the central pixel increases.

10. 3D Analysis

Figure 1B:
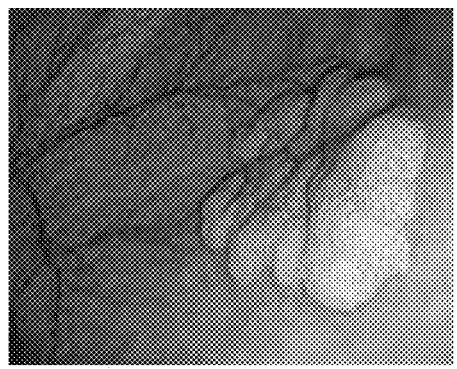

Tissues, which are suspected as polyps, are usually different in their 3D structure from its nearest environment and from the regular textural pattern of the colon in general (see FIG. 1A). This is usually true, although in a less salient way, also for flat polyps (see FIG. 1B).

Taking a sequence of images from the video frames when the endoscope camera is moving enables to estimate the 3D structure of the suspected area and its environment by means such as Structure From Motion (SFM, see p. Koenderink, J. J., & Van Doom, A. J. (1991). Affine structure from motion. JOSA A, 8(2), 377-385), Stereo analysis by correspondence and disparity values (see q. Scharstein, D., & Szeliski, R. (2002). A taxonomy and evaluation of dense two-frame stereo correspondence algorithms. International journal of computer vision, 47(1-3), 7-42), and Epipolar geometry (see r. Laveau, S., & Faugeras, O. (1994, October). 3-D scene representation as a collection of images. In Pattern Recognition, 1994. Vol. 1-Conference A: Computer Vision & Image Processing., Proceedings of the 12th IAPR International Conference on (Vol. 1, pp. 689-691). IEEE).

The 3D analysis algorithm of the invention uses the above mentioned techniques for 3D analysis, in parallel and in several steps, and up to a scale, so the intresic and extensic parameters of the camera are not needed, and mostly the local irregularities in the depth of the colon surface are identified in order to find bulged regions which might be suspected as polyps. With endoscopes that are able to project or present an in advance a known, predetermined pattern on the colon surface, this pattern can be seen in the image, and then the scale can be set and the actual 3D value can be calculated (as well as the internsic an extrinsinc parameters of the camera can be estimated) on the fly. The algorithm uses camera ego-motion calculation, which is supplied by supportive algorithm which tracks features in the colon, in order to estimate the extrinsic changes between the frames it uses for the 3D (or semi-3D) reconstruction.

For example, one of the 3D analysis algorithms looks for deviations and singularities in the generated 3D map (or semi-3D map such as the disparity map) which create salient and acute 3D edges (discontinuation in the 3D data) and which are not typical to the internal folds of the colon. Another algorithm looks for dense changes (high frequencies) in the 3D or (semi 3D map). The polyp region is distinguished from the rest of the regions since of dense changes in the disparity map in its region, these changes are typical to this type of polyp since of its complex and repeated texture which causes local and small error in the correspondence calculations and therefore small and local random-like changes of 5 to 15 pixels in the resulted in disparity map. The correspondence between frames is calculated in several ways, such as, by feature based correspondence (between features extracted from both images by a feature extraction method) and by image based correspondence by methods such as stereo correspondence and optical flow algorithm.

The stereo disparity map is more effective when the movement of the scope is mainly translation in the image plane, while the optical flow motion field calculation and the feature-based correspondence are more tolerant for general movements of the scope between taking the frames which are used by the 3D algorithms. In the system, the general 2D homogenous rigid body (with scaling) transformation matrix which describes the movement of the camera is first calculated from the results of the feature based correspondence and the optical flow algorithms and this matrix, when the translation elements in it are set to zero, are used to correct the images which are fed to the stereo algorithm in a way that mainly 2D translation in the camera image plane is the difference between the two input images.

The system uses the SURF's features, optical flow and stereo matching in order to produce 3D clues needed by the system. The main steps are to calculate in parallel an optical flow algorith, and Speed Up Robust Features (SURF) or Scale-Invariant Features Transform (SIFT) features correspondence in order to estimate the camera motion matrix between the two frames, and then set the translation in the matrix to zero, warp one image to other according to the motion matrix (without translation), and use the translation difference which was left to calculate the disparity map between the images, which is base for the 3D differences in the image.

In the analysis of the 3D clues by the system, it is taking in consideration that the endoscopic images of the colon tissue are taken from very close distance. When taking images from such a close distance, there are several issues that need to be considered, such as Geometric deformations which usually get prominent only from a very close distance and also relatively high influence of even small camera movements. Also, the influence of wide angle lens is taken into consideration by using in advance calibration in order to rectify the diverged image. The typical deformation is usually higher at the periphery of the image and deforms a straight line in the image to a curved concave or convex line with a maximum deviation from the original straight line of to 10%-15% of the image width or height.

Figure 6:
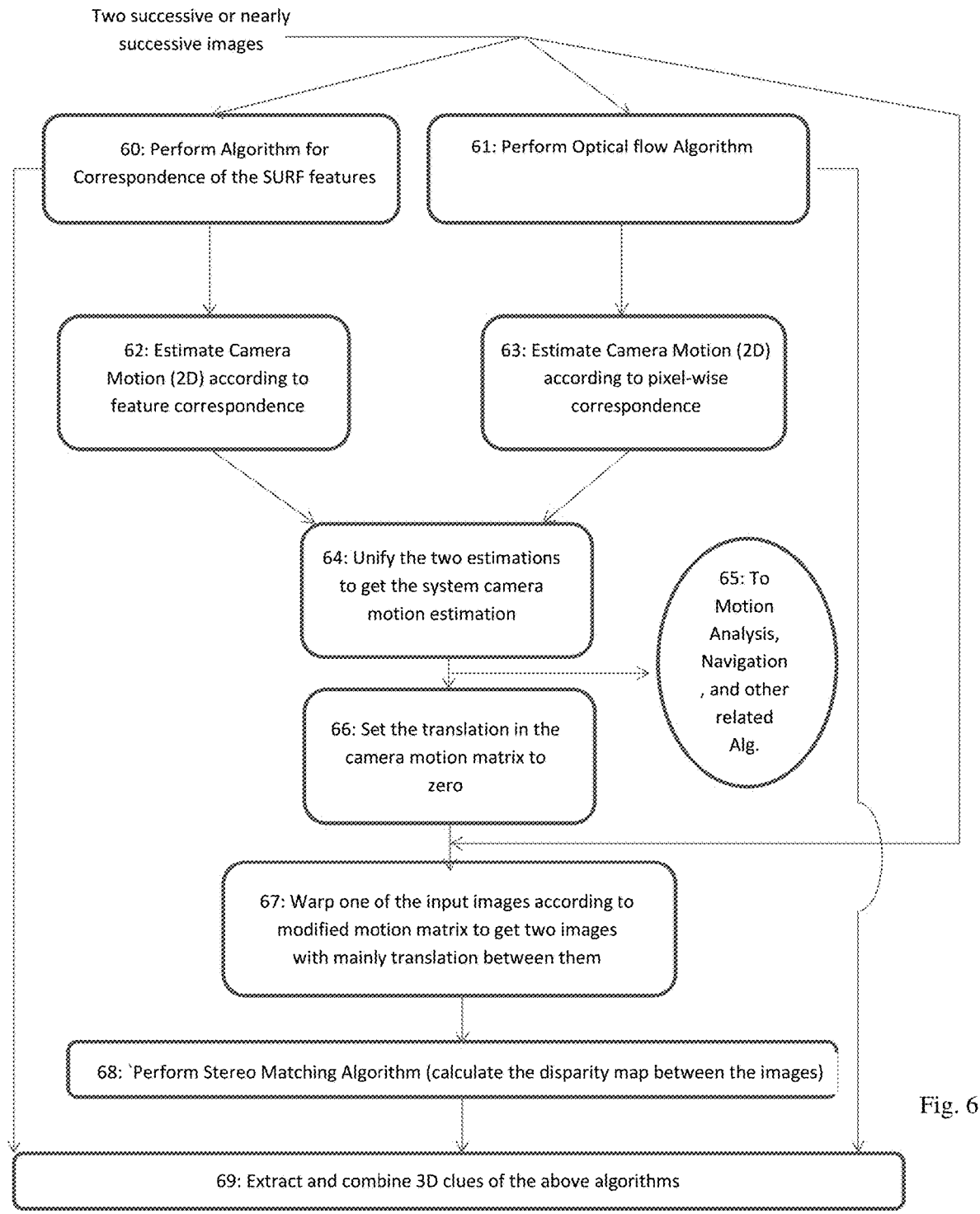
FIG. 6 is an embodiment of a flowchart showing the use of the SURF's features, optical flow and stereo matching in order to produce 3D clues needed by the system.

Reference is now made to FIG. 6 is an embodiment of a flowchart showing the use of the SURF's features, optical flow and stereo matching in order to produce 3D clues needed by the system. In step 60 the SURF feature are compared between successive images. In step 61, the optical flow is calculated between successive images. In step 62, the camera motion is estimated in accordance with step 60. In step 63, the camera motion is estimated in accordance with step 61. In step 64, the two estimations are combined to produce one estimation. In step 65, the camera motion matrix is transferred to algorithms that require it such as the tracking and navigation algorithms. In step 66, the translation component in the camera motion is set to zero. In step 67, one image is warped to the other (except for the translation which was set to zero). In step 68, stereo matching algorithm is applied on the two "translated" images in order the 3D values from them. In step 69, 3D clues from the processed algorithms (described above) are extracted and combined in order to be used by the system.

Figure 7A:
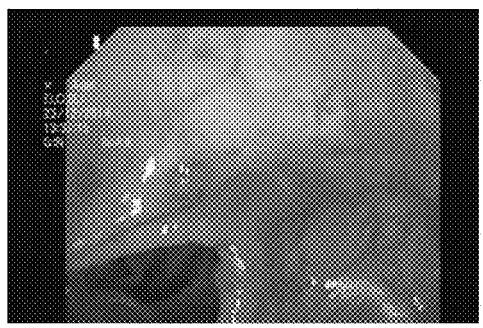
FIGS. 7A-7F are an example of results of the algorithm for boundary Analysis for detection of closed-shape bumped polyps according to their 3D shading.
Figure 7B:
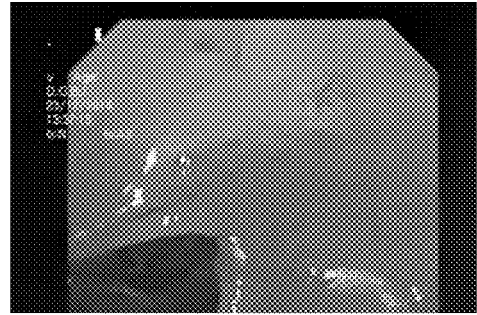
Figure 7C:
Figure 7D:
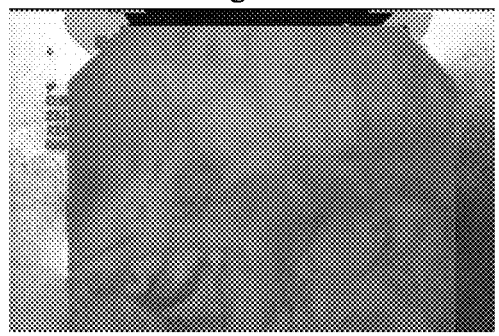
Figure 7E:
Figure 7F:
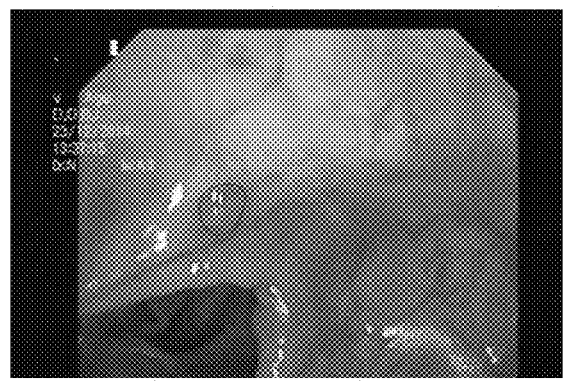

3D clues are also extracted from one image, by using shading (Structure From Shading, SFS) and illumination patterns which are typical to different types of polyps. An example of the results of an algorithm which analyzes the shading boundaries is shown in FIGS. 7A-7F. Once a bump region is detected, its probability to be decided as a suspicious polyp region is increased, namely, less confidence is needed from the other detection sub-methods in order to finalize the decision on it as a suspicious region. In some working points of the system (see above definition) a decision of a region, with high confidence, as a bump, would be sufficient to finalize the decision on it as a suspicious region. FIGS. 7A-7F are an example of results of the algorithm for boundary Analysis for detection of closed-shape bumped polyps according to their 3D shading. FIG. 7A is the original image, FIG. 7B is the original image without the shading (was omitted by a Retinex algorithm), FIG. 7C is the color difference between the original image and image without the shading and FIG. 7D is the gray level difference between the original image and the image without the shading, FIG. 7E is binarization of this difference (of the shading element in the image) and FIG. 7F is the sign of the region, that was detected according to further evaluation of the binary image for pattern which can correspond to closed shape bumped polyp, on the original image.

11. Motion Analysis

The camera motion calculation algorithm is mainly based on optical flow and motion matrix calculated from feature correspondence (see step 60 in FIG. 6). The calculated camera motion is then used further by the 3D algorithms of the system, and also by additional related algorithms:

The system keeps tracking of the endoscope movement in the colon to create navigation map. This helps, when pulling the endoscope out the colon, to alarm when the endoscope tip is in the region of tissue that were estimated as suspicious (or where landmarked manually or automatically) when the endoscope was pushing into the colon, and to create a visual and graphical map of the colon and where special things where detected, landmarked or occurred.

According to the movement of the endoscope, the system can identify if the operator stopped the fluent movement of the endoscope when suspicious tissue or polyp was detected, and thus to estimate whether this polyp or suspicious tissue was missed or not.

According to the movement of the camera, the system can calculate several statistics about the performed colonoscopy, such as the speed of movement in each of colon parts during entering the colon and during exiting the colon.

Also, from the camera movement analysis, calibration data about successive or nearly successive images for the 3D algorithms can be produced.

Supervised Machine Learning-Based Detectors

12. Convolutional Neural Network (CNN) Based Detectors

One of the main detectors in the system is based on CNN. It has Several Convolutional layers (each layer is followed by activation and polling layer), several fully connected layers, and at the end soft-max layer to classify between polyp and non-polyp regions. The network does its training (and predications) either on patches or on the entire video frame and can perform either detection only if a polyp exists in the image, or to detect its location in the image and segment it (find its border contour). The main novelty by using this network is the specific architecture of its CNN (see FIG. 8) which, inter alia, enables to add conventional found features to the semantic layers (the fully connected layers) and thus to expand these layers, and to use ensamble of such CNN's (based on RGB of the image, first and second derivatives of the image and successive presentations of the image or its patches) to detect or segment polyp, and more than this, the massive use of data augmentation (scaling, rotating, flipping, and color shift in the H channel of the HSV format, and making artificial collages of polyps and background) in order to compensate for the potential absence of massive amount of data of the endoscopic procedure which usually are not recorded and are much less prevalent than natural images or other imaging data. In addition, using the conventional algorith, to select candidate patches or regions to be fed to the CNN's and filter out the rest, and instead of feeding just the candidate patch, feeding several sampled patches from its environment, is novel, and unique to the need of detecting polyps whom their border is in many cases vague and assimilated within their surroundings. CNN detection can be based also on Segmetation CNN's such as Mask RCNN or fully convolotional CNN (CNN's without the fully connveted layers at the end).

The use of the CNN is also accompanied by post processing (masking irrelevant regions from the image for example, and discarding unfocused images), as well as post processing for morphological and time consistency decisions on whether a region that was detected by the network is actually being decided as a polyp.

The basic structure of the network is also accompanied by recurrent elements in the time (RNN and LSTM-RNN for special treatment for video images) and recurrent elements in the space (RCNN and 2DLSTM for segmentation).

The supervised learning classifiers and detectors are based on Decision Trees, Random forest, Support Vector Machine (SVM), all might be enhanced by Boost technique, Convolutional Neural Network (CNN) and Regional CNN (RCNN) for patch-wise based CNN processing, and Long-Short Term Memory Recurrent CNN (LSTM Recurrent CNN), with combination of pre-extracted features fed either into the fully connected layers of said deep machine-learning-based networks as additional feature, or into the input conventional layer as additional image channel; The CNN will usually work on patches, although it can work also on the whole frame if detecting whether the frame includes polyp or does not is sufficient task or if RCNN is applied to imitate the division to patches. An example of the CNN architecture which is used by the system is shown in FIG. 8.

Figure 8:
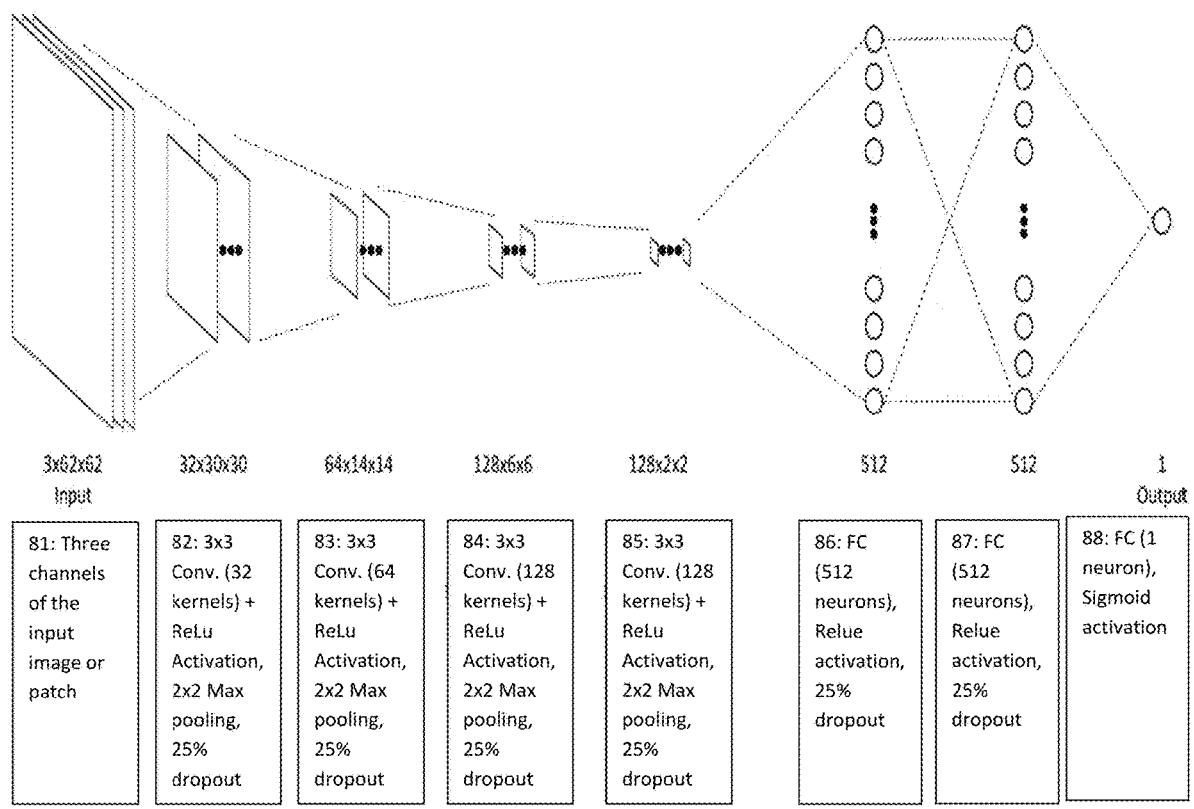
FIG. 8 shows an example of a CNN architecture used by the system.

FIG. 8 shows an example of the CNN architecture which is used by the system. Block 81 is the three channels of the input image (a 62×62 patch in this case). Block 82 is the first convolutional layer which includes 32 convolution kernels of size of 3×3, followed by ReLu activation layer which is also followed by a 2×2 max pooling layer and in which 25% of the output pixels are dropped out. Block 83 is the second convolutional layer which includes 64 convolution kernels of size of 3×3, followed by ReLu activation layer which is also followed by a 2×2 max pooling layer and in which 25% of the output pixels are dropped out. Block 84 is the third convolutional layer which includes 128 convolution kernels of size of 3×3, followed by ReLu activation layer which is also followed by a 2×2 max pooling layer and in which 25% of the output pixels are dropped out. Block 85 is the fourth convolutional layer which includes 128 convolution kernels of size of 3×3, followed by ReLu activation layer which is also followed by a 2×2 max pooling layer and in which 25% of the output pixels are dropped out. Block 86 is the first fully connected layer which includes 512 neurons (features of the patch) followed by a ReLu activation layer and in which 25% of the output pixels are dropped out. Block 87 is the second fully connected layer which includes 512 neurons (features of the patch) followed by a ReLu activation layer and in which 25% of the output pixels are dropped out. Block 88 is an activation layer with a single Sigmoid activation neuron which is normalized output is the probability of the patch to include or to be included in a polyp.

The three channels of the image (the third dimension of the input images which is of size of three—the three channels) which are fed to the network in FIG. 8 as an input (the input images are depicted on the left of FIG. 8) can be selected. In some embodiments, the system uses an ensemble of CNN's which are fed by patches of the image instead of full frames in order to enhance the local behavior of the computation.

In some embodiments, the system uses a first CNN which works on the RGB channels of the image, a second CNN which works on the first and second derivatives of the intensity channel of the image (for example, Sobel derivatives, Laplacian of Gaussian operator, and Canny edge detector), and a third CNN which works on three successive time occurrence of the patch or the image to let the network take in consideration the continuity of the polyp or suspicious region appearance. The results of the three networks are unified to one decision based on max operator, or any type of weighted average which its weight parameters can be learned together and in parallel with the learning process of the three CNN's. If LSTM recurrent CNN is used, then the third CNN of the time successive patches or frames can be discarded.

To the first fully connected layer in FIG. 8 (which is a semantic layer which represents features that were extracted by the network) of each CNN, additional features, extracted by the conventional (unsupervised) detectors, can be added to extend this layer and the fully connected layer which follow it. Also, the unsupervised detectors can be used in order to filter out patches from the input of the CNN's which works on patches. In this case, for each candidate patch (a patch which was not filtered out), several patches in its close environment would be sampled to represent it as an input to the CNN's. Also, specific regions might be discarded in advance by the preprocessing algorithms such as lumen detection (a region which shall be filtered out) and the unfocused region detection (which might also discard complete frame if most of it is unfocused). Those preprocessing filtering algorithm can also be implemented by Decision Trees, Random Forest or SVM (when the input to each method would be relevant features which were first extracted (such as SIFT features or Hessian Kernel based features) and which can teach about the existence of Lumen or unfocused region. A specific CNN (in the architecture of FIG. 8 for example) can also be taught to detect and segment Lumen or Unfocused regions in the image. The Decision Trees, Random Forest and SVM, can also operate in parallel to the main three CNN's on features that were first extracted, such as SIFT, SURF, Hessian Kernels, Sobel operator, in order to decide if a patch or image contains a polyp or suspicious region.

All the supervised algorithm supply, by inheritance from the way they work, a confidence level (either for the whole frame or for the patch) which represent the probability of this frame or patch to include or to be included in a polyp or suspicious region. A tuned threshold level actually decides which frames or patches (with what confidence level) would be transfer for the further process of the post processing as candidates for polyp or suspicious regions (a typical value might be 0.85 when confidence value changes between 0 to 1).

The combination of the conventional (unsupervised) detectors and supervised learning detectors and classifiers actually decides if the system can cope with just notifying if a frame contain a polyp, or also locate and segment the polyp in the frame. At least two conventional detectors and one supervised machine learning method are needed to be integrated together in order to notify if there is a polyp or suspicious region in the frame, and at least three conventional detectors and two supervised machine learning methods are needed to be integrated together in order to locate and segment the polyp or suspicious regions in the frame.

13. Postprocessing:

In the post processing, after the decision of the detector and classifiers which suggested whether or where a polyp or suspicious region can be in the image, the suggestions are further examined. They are examined by blob analysis on the results of the detectors and classifiers on the frame or patches (conventional detector can work on the whole image, Decision Trees, Random forest and SVM would better work on patches, and CNN must work on patches unless a RCNN is used) and then according to morphological criteria such as the size of the suggested regions and their closeness to the image border, it compactness (the ratio between its area to its convex-hull area), its eccentricity (the ratio of the distance between the foci of the ellipse, that has the same second moments as the region, and its major axis length), according to the average, the minimum, the maximum, and the change in the level of confidence of each pixel in the blob derived from the unified decision of the detectors and classifiers in the level above, and according to time consistency of the results. The blob analysis cleans sporadic regions in the image by tools such as spatial median filtering. Time consistency analysis cleans sporadic regions in the time domain by tools such temporal median filter.

The post processing can also limit the number of polyp or suspicious regions which may be expected to be found in a single frame. The post processing can also be impalement by the supervised machine learning methods, to learn the correlation between the detectors and classifiers working point (according to the selected threshold mentioned above) and the ground truth data on polyp existence and location in the frame. The post processing can work on unified decision of all the detectors and classifier and then it would actually function as the decision making unit of the system, or it can work on separate groups of detectors and classifiers, and additional decision making unit might be needed in order to take the final decision per frame or successive frames, and this decision making unit can actually operate in similar way to the post processing method which described herein, and might get the assistance of predefined rules (rule-based decision making assistance) such as that it is needed that at least 2 of the 3 groups from the level above shall be decide that a polyp or suspicious region exist in order to finally decide that it exists.

If the system is set just to notify if a polyp or suspicious region exist in the frame, then once at list acceptable polyp or suspicious region was detected the system would give a notification on it. If the system is set and tuned to give also the location and borders (segmentation) of the polyp or suspicious regions, then a more accurate process is needed, and therefore more conventional (unsupervised) and supervised detectors and classifiers are needed to be integrated together (as mentioned above) and system will give also indication on the polyp or suspicious region location and borders.

14. Polyp Size Calculation and Polyp Type Classification

There are several ways to measure a polyp size. In general, the algorithm for polyp size is based on the 3D estimation of the system which adds a depth information. In most of the algorithms in the system only a semi-3D reconstruction is used, not a full depth value is calculated. For the polyp size calculation, a full 3D reconstruction is calculated. For this, several unique non-calibrated 3D reconstruction algorithms are used. An example of non-calibrated 3D reconstruction algorithm is shown in Torresani, Lorenzo, Aaron Hertzmann, and Christoph Bregler. "Learning non-rigid 3d shape from 2d motion." *Advances in Neural Information Processing Systems,* 2003. When it is possible, and at least some of the camera intrinsic parameters are known, those parameters support the non-calibrated reconstruction algorithm to get accurate results. There is also the possibility to enter through the endoscope channels a calibration tool, or to project from the endoscope device to the colon tissue a known pattern in order to get more accurate results from the non-calibrated reconstruction algorithms.

The polyp size calculation algorithms are used also to make on demand specific measurements of desired anatomy or specific tissue in the colon—it is done by measuring the actual distance, in 3D, between two points signed on the image, or measuring the actual radii or periphery or area of a circle, ellipse, or rectangle marked on the image.

The polyp type can be classified between predefined classes by means of supervised machine learning methods such as SVM, Decision Trees, Random forest, and deep machine learning methods such as CNN and its derivative. Those methods shall be fed as an input by regions (or features from regions) that were detected, either automatically or manually as polyps, and during their supervised learning phase they shall get feedback (ground truth data) on the actual type of those regions.

15. The Device/System

Some embodiments comprise a software that can be run on any laptop, desktop, tablet, or mobile computerized device which gets video online from the video output of the colonoscopy device. This online add-on device, which is connected to the colonoscopy device via the video-out channel of the colonoscopy device, can be backed-up with a server with high computation capability and be connected to it via an Ethernet connection.

The colonoscopy device can have several presentations mode (for example enhanced or non-enhanced mode) which affects also its video out. Therefore the device of the invention shall have, in its preprocessing level, a module which will guess the mode of the colonoscopy device to which it is attached, by performing some statistical analysis on the images which it gets from the colonoscopy device' video out channel.

The software can also be run on a computerized stand-alone device which analyzes an offline video which was recorded from a colonoscopy device.

It can also run as an algorithmic software which is embedded in the colonoscopy device with the appropriate Graphical User Interface (GUI).

The output of the computerized device is indications, online or offline of potential locations in the video which are suspicious as suspicious tissues (polyps in colonoscopy procedure). These indications serve as recommendations for the examiner/technician/physician running the medical procedure to look for suspicious regions or polyps in the areas marked by the system.

The computerized device receives the video output from the endoscopy/colonoscopy main device either via the main channel or via a secondary channel, processes it, and presents it either on the main screen or on a secondary screen. The computerized device has a control unit, preferably a remote control unit to control, which controls its functionality. An example of the device functionality is whether to process the video or just to convey it to the screen, whether to present the process results or not, what level of confidence shall be the minimum for presentation, controlling the sensitivity and specificity of detection of the detection, operating specific functions such as polyp size calculation, complete polyp removal verification, whether to record the video with the detection results with it, creating a recorded video with indexing, or a shortened recorded essence of the whole real-time video, which includes only the frames with suspicious colon tissue regions, and so on. The warning of the detected suspicious regions can appear as overlay over the original video, or/and in other ways such as warning sounds, flashing light and etc. The device has also a mode of self-contained working (independent mode or offline mode) in which it can be fed by a recorded video from the colonoscopy procedure and operate on it in as a similar way as it operates on real-time video. In this mode, the time constraints on the running algorithms can be somewhat released since the recorded video can be fed more slowly and a more exhaustive version of the different algorithms can be used in order to achieve better detection results. Also, the minimum threshold, or the minimum confidence, for presenting a region as suspicious, can be decreased (to get a lower minimum threshold) since those suspicious regions can be reviewed later by the expert in order to decide whether it is a polyp or not, and this is in contrast to the real time warning on suspicious regions for which the physician shall react immediately during the procedure.

The sensitivity of the device is the true positive rate (the complement of the false negative rate) and in the device's algorithmic system it is the rate of correct polyp detection. The specificity of the device is the true negative rate (the complement of the false positive rate) and in the device's algorithmic system it is the rate of correct detection of non-polyp region. The online algorithms for calculating the confidence of Although the invention has been described in detail, nevertheless changes and modifications, which do not depart from the teachings of the present invention, will be evident to those skilled in the art. Such changes and modifications are deemed to come within the purview of the present invention.

It will be readily apparent that the various methods and algorithms described herein may be implemented by, e.g., appropriately programmed general purpose computers and computing devices. Typically a processor (e.g., one or more microprocessors) will receive instructions from a memory or like device, and execute those instructions, thereby performing one or more processes defined by those instructions. Further, programs that implement such methods and algorithms may be stored and transmitted using a variety of media in a number of manners. In some embodiments, hard-wired circuitry or custom hardware may be used in place of, or in combination with, software instructions for implementation of the processes of various embodiments. Thus, embodiments are not limited to any specific combination of hardware and software.

A "processor" means any one or more microprocessors, central processing units (CPUs), computing devices, microcontrollers, digital signal processors, or like devices.

The term "computer-readable medium" refers to any medium that participates in providing data (e.g., instructions) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Bluetooth, TDMA, CDMA, 3G.

Where databases are described, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models and/or distributed databases) could be used to store and manipulate the data types described herein. Likewise, object methods or behaviors of a database can be used to implement various processes, such as the described herein. In addition, the databases may, in a known manner, be stored locally or remotely from a device which accesses data in such a database.

The present invention can be configured to work in a network environment including a computer that is in communication, via a communications network, with one or more devices. The computer may communicate with the devices directly or indirectly, via a wired or wireless medium such as the Internet, LAN, WAN or Ethernet, Token Ring, or via any appropriate communications means or combination of communications means. Each of the devices may comprise computers, such as those based on the Intel® Pentium® or Centrino™ processor, that are adapted to communicate with the computer. Any number and type of machines may be in communication with the computer.

The invention claimed is:

1. An image processing system connected to the video output of an endoscopy device during an endoscopic procedure, comprising:
    at least one processor; and
    at least one memory communicatively coupled to the at least one processor comprising computer-readable instructions that when executed by the at least one processor cause the image processing and machine learning system to implement a method of detecting in real-time suspicious regions in endoscopic video images produced by the endoscopy device, the method comprising performing the following steps on a plurality of successive video frames:
    (i) applying on each of said video frames or portions of said frames a deep machine-learning-based detection networks process comprising one or more models of general type of Detection Convolutional Neural Network (Detection CNN), Regional CNN (RCNN), Faster Regional CNN (FRCNN), You Only Look Once (YOLO) CNN, Small Data Driven (SDD) CNN, and Patch-Wise Classification CNN followed by post processing of region or blob detection, wherein each model receives as input color channels of original frames or images resulting from the processing of said conventional algorithms or three successive frames; or any combination thereof, wherein the determination to identify an area as a suspicious region takes into account the identification of that region in a predetermined number of successive frames;
    (ii) receiving the results of (i) and reaching a final decision about the suspicious regions existence and location in the frame according to one or more predetermined rules, including rules which based on spatial and temporal analysis;
    (iii) identifying one or more video frames as containing one or more suspicious areas and pointing out the suspicious areas' locations in each frame; and
    (iv) tracking the endoscope tip movements according to the changes in the images of successive frames of the video stream, which comes from the camera at the endoscope tip, and by using the sequence of registered images, calculating the portion of the internal part of the colon which was covered by the camera's visual field.

2. The system according to claim 1, further comprising the step of applying on each of said video frames or portions of said frames a deep machine-learning-based detection networks process comprising one or more models of general type of Segmentation Convolutional Neural Network (Segmentation CNN), Mask RCNN, Semantic Segmentation CNN such as DeepLab, Fully Convolutional CNN, wherein the location of each suspicious area is defined by the bounding box of the segmentation of the suspicious area, and the suggested resection contour of each suspicious area is based on the contour of the segmentation of the suspicious area.

3. The system according to claim 1, further comprising performing one or more of the following steps:
    (i) removing from each frame peripheral regions outside the visual feed of the endoscope camera;
    (ii) identifying and removing feces regions in a frame;
    (iii) identifying areas with liquids in each frame or portion of frame and removing these areas or the whole frame from further processing;
    (iv) identifying surgical tools in each frame or portion of frame and removing these areas or the whole frame from further processing; and
    (v) identifying blurry regions in each frame or portion of frame and removing these areas or the whole frame from further processing.

4. The system according to claim 3, wherein removing from each frame peripheral regions outside the visual feed of the endoscope camera is done by finding uniform color and low intensity regions at the peripheral part of the frame and using a region growth algorithm and morphological verification criteria.

5. The system according to claim 3, wherein feces regions are identified by identifying yellowish regions with a morphology of stain which are not bulging from the surrounding surface where thresholds and limits of the intensity, color and saturation for identifying such regions are adaptively calculated.

6. The system according to claim 1, using the identified boundaries of the suspicious areas, and further comprising the step of marking the suspicious area using an overlay marking on a dedicated display area, wherein said marking comprise marking the type or size or confidence level of the suspicious region by a color marking or additional marking attributes.

7. The system according to claim 1, wherein the existence of suspicious regions.

8. The system according to claim 1, further comprising the step of classifying the suspicious regions according to predefined types.

9. The system according to claim 1 where the tracking results are incorporated in the temporal analysis of the final decision in order to improve the confidence of the detection of the suspicious areas.

10. The system according to claim 1, further comprising the step of registering a specific location of the endoscope tip by a user landmark and signaling when the endoscope tip is returning to the landmark location.

11. The system according to claim 10, further comprising the step where instead of user landmark, the location of the endoscope tip, when a suspicious region is detected but not treated, is registered, and signaling when the endoscope tip is returned to this location.

12. The system according to claim 1, further comprising the step of identifying if a suspicious region was treated by verifying if surgical tools were identified in successive frames; or identifying if a suspicious region was noticed and examined according to the length of time said suspicious region appeared along successive frames.

13. The system according to claim 1, wherein suspicious regions, frames with suspicious region, and irrelevant frames are identified in an off-line recorded video.

14. The system according to claim 1, further comprising the step of calculating statistics regarding the endoscopic procedure.

15. The system according to claim 14, wherein said statistics comprise the total time of the procedure, time to the cecum and from the cecum, how many suspicious regions were detected, and how many suspicious regions were removed during the procedure.

16. The system according to claim 1, wherein data augmentation is used for deep machine-learning-based networks processes in order to use polyp and background characteristics in order to create from each frame or patch several additional frames to be processed by deep learning networks.

17. The system according to claim 1, further comprising the step of adding pre-extracted features provided by the conventional algorithms into the fully connected feature layers of said deep machine-learning-based networks as additional features of said layers.

18. The system according to claim 1, wherein the suspicious regions are polyps or cancerous regions.

19. An image processing system connected to the video output of an endoscopy device during a colonoscopy procedure, comprising:
at least one processor; and
at least one memory communicatively coupled to the at least one processor comprising computer-readable instructions that when executed by the at least one processor cause the image processing and machine learning system to implement a method of detecting in real-time polyps in endoscopic video images produced by the endoscopy device, the method comprising performing the following steps on a plurality of successive video frames:
(i) applying on each of said video frames or portions of said frames a deep machine-learning-based detection networks process comprising one or more models of general type of Detection Convolutional Neural Network (Detection CNN), Regional CNN (RCNN), Faster Regional CNN (FRCNN), You Only Look Once (YOLO) CNN, Small Data Driven (SDD) CNN, and Patch-Wise Classification CNN followed by post processing of region or blob detection, wherein each model receives as input color channels of original frames or images resulting from the processing of said conventional algorithms or three successive frames; or any combination thereof, wherein the determination to identify an area as a suspicious region takes into account the identification of that region in a predetermined number of successive frames;
(ii) receiving the results of (i) and reaching a final decision about the suspicious regions existence and location in the frame according to one or more predetermined rules, including rules which based on spatial and temporal analysis;
(iii) identifying one or more video frames as containing one or more suspicious areas and pointing out the suspicious areas' locations in each frame; and
(iv) tracking the endoscope tip movements according to the changes in the images of successive frames of the video stream, which comes from the camera at the endoscope tip, and by using the sequence of registered images, calculating the portion of the internal part of the colon which was covered by the camera's visual field.

* * * * *